United States Patent
Gromotka et al.

(10) Patent No.: US 11,747,651 B2
(45) Date of Patent: Sep. 5, 2023

(54) COMPUTER-IMPLEMENTED METHOD FOR DETERMINING CENTRING PARAMETERS FOR MOBILE TERMINALS, MOBILE TERMINAL AND COMPUTER PROGRAM

(71) Applicant: Carl Zeiss Vision International GmbH, Aalen (DE)

(72) Inventors: Jeremias Gromotka, Aalen (DE); Michael Gamperling, Leipheim (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/056,763

(22) Filed: Nov. 18, 2022

(65) Prior Publication Data
US 2023/0077539 A1    Mar. 16, 2023

Related U.S. Application Data

(63) Continuation of application No. PCT/EP2021/062313, filed on May 10, 2021.

(30) Foreign Application Priority Data

May 22, 2020    (EP) .................................... 20176093

(51) Int. Cl.
*G02C 7/02*        (2006.01)
*G06T 7/70*        (2017.01)
(Continued)

(52) U.S. Cl.
CPC ............ *G02C 7/027* (2013.01); *G02C 13/003* (2013.01); *G06T 7/60* (2013.01); *G06T 7/70* (2017.01);
(Continued)

(58) Field of Classification Search
CPC .... G02C 7/027; G02C 13/003; G02C 13/005; G06T 7/60; G06T 7/70; G06T 17/00; G06T 2207/30201; A61B 3/111
(Continued)

(56) References Cited

U.S. PATENT DOCUMENTS 7,950,800 B2    5/2011    Nauche et al.
8,360,580 B2    1/2013    Chauveau
(Continued)

FOREIGN PATENT DOCUMENTS

| DE | 102011009646 A1 | 8/2012 |
| EP | 3355214 A1 | 8/2018 |
| WO | 2015101737 A1 | 7/2015 |

OTHER PUBLICATIONS

DIN EN ISO 7998:2006-01 "Augenoptik—Brillenfassungen—Auflistung äquivalenter Begriffe und Vokabular [Ophthalmic optics—Spectacle frames—Lists of equivalent terms and vocabulary]," DIN Deutsches Institut fur Normung e.V., Jan. 2006, and English-language machine translation thereof.

(Continued)

*Primary Examiner* — Tuyen Tra
(74) *Attorney, Agent, or Firm* — Tautz & Schuhmacher LLC; Georg Hasselmann

(57) ABSTRACT

Methods and devices for determining at least one centring parameter are disclosed. A mobile terminal is moved from a first position to a second position, and a respective image is captured of an eye area of a person. The acceleration is also measured during the movement. The centring parameter is then determined based on the captured image and the measured acceleration.

17 Claims, 6 Drawing Sheets

(51) Int. Cl.
 G02C 13/00 (2006.01)
 G06T 7/60 (2017.01)
 G06T 17/00 (2006.01)
(52) U.S. Cl.
 CPC .... *G06T 17/00* (2013.01); *G06T 2207/30201* (2013.01)
(58) Field of Classification Search
 USPC ....... 351/41, 159.01, 159.73, 159.74, 159.75
 See application file for complete search history.

(56) References Cited

U.S. PATENT DOCUMENTS

| | | | |
|---|---|---|---|
| 8,459,792 B2* | 6/2013 | Wilson | A61B 3/111 351/204 |
| 9,535,270 B2 | 1/2017 | Divo et al. | |
| 9,928,421 B2 | 3/2018 | Thomet et al. | |
| 9,971,172 B2 | 5/2018 | Cabeza-Guillen et al. | |
| 10,702,149 B2* | 7/2020 | Limon | A61B 3/111 |
| 10,859,859 B2 | 12/2020 | Nieuwenhuis et al. | |
| 2013/0076884 A1 | 3/2013 | Choukroun | |
| 2013/0083976 A1 | 4/2013 | Ragland | |
| 2013/0194253 A1 | 8/2013 | Ohmi | |
| 2018/0140186 A1 | 5/2018 | Limon | |
| 2019/0196221 A1 | 6/2019 | El-Hajal et al. | |

OTHER PUBLICATIONS

DIN EN ISO 8373:2012 "Robots and robotic devices—Vocabulary," English and French version, 2012.
DIN EN ISO 13666:2012 "Ophthalmic optics—Spectacle lenses—Vocabulary (ISO 13666:2012)," German and English version, Oct. 2013.
DIN EN ISO 8624 "Augenoptik—Brillenfassungen—MaBsystem und Begriffe [Ophthalmic optics—Spectacle frames—Pleasuring system and terminology] (ISO 8624:2015)," German version EN ISO 8624:2015, Dec. 2015, and English-language machine translation thereof.
Internet citation "Augendrehpunkt [center of rotation of the eye]," available at https://www.spektrum.de/lexikon/optik/augendrehpunkt/264, 1999, last accessed Jan. 26, 2023, and English-language machine translation thereof.
Jung et al., "Camera trajectory estimation using inertial sensor measurements and structure from motion results," in Proceedings of the IEEE Computer Society, Conference on Computer Vision and Pattern Recognition, vol. 2, pp. II-732-II-737, 2001.
Kim et al., "A Fast Center of Pupil Detection Algorithm for VOG-Based Eye Movement Tracking," Proceedings of the 2005 IEEE Engineering in Medicine and Biology 27th Annual Conference Shanghai, China, Sep. 1 to 4, 2005.
Asadifard et al., "Automatic Adaptive Center of Pupil Detection Using Face Detection and CDF Analysis," Proceedings of the International MultiConference of Engineers and Computer Scientists 2010 vol. I, IMECS 2010, Hong Kong, Mar. 17 to 19, 2010.
Sachs, "Sensor Fusion on Android Devices: A Revolution in Motion Processing," Google Tech Talk available at https://www.youtube.com/watch?v=C7JQ7Rpwn2k&feature=youtu.be), uploaded Aug. 2, 2010, 20 sample screen shots submitted, last accessed Jan. 11, 2023.
G. Nützi et al., "Fusion of IMU and Vision for Absolute Scale Estimation in Monocular SLAM," Journal of Intelligent & Robotic Systems, vol. 61, pp. 287-299, 2011.
Wikipedia encyclopedia entry "Triangulation (Messtechnik) [Triangulation (metrology)]," available at https://de.wikipedia.org/w/index.php?title=Triangulation_(Messtechnik)&oldid=220151489, last edited Feb. 13, 2022, and English-language counterpart entry thereof, last accessed Nov. 16, 2022.
Wikipedia encyclopedia entry "Simultaneous Localization and Mapping," available at https://de.wikipedia.org/wiki/Simultaneous_Localization_and_Mapping, last edited Apr. 27, 2021, and English-language counterpart entry thereof, last accessed Jan. 26, 2023.
Extended European Search Report issued in EP 20 176 093.1, to which this application claims priority, dated Oct. 23, 2020, and English-language translation thereof.
International Search Report issued in PCT/EP2021/062313, to which this application claims priority, dated Jul. 12, 2021, and English-language translation thereof.
Written Opinion issued in PCT/EP2021/062313, to which this application claims priority, dated Jul. 12, 2021.
International Preliminary Report on Patentability issued in PCT/EP2021/062313, to which this application claims priority, completed Aug. 2, 2022, and English-language translation thereof.

* cited by examiner

COMPUTER-IMPLEMENTED METHOD FOR DETERMINING CENTRING PARAMETERS FOR MOBILE TERMINALS, MOBILE TERMINAL AND COMPUTER PROGRAM

CROSS REFERENCE TO RELATED APPLICATIONS

This application is a continuation application of international patent application PCT/EP2021/062313, filed May 10, 2021, designating the U.S. and claiming priority to European patent application EP 20 176 093.1, filed May 22, 2020, both of which are hereby incorporated by reference in their entireties.

TECHNICAL FIELD

The present application relates to computer-implemented methods for determining centration parameters for a mobile terminal, corresponding mobile terminals and computer programs.

BACKGROUND

A mobile terminal should be understood to mean a device which comprises at least one programmable processor, a display, and also a camera and an acceleration sensor, and which is designed to be carried, i.e., is configured in respect of dimensions and weight so that a person is capable of carrying it along. Typical examples of such mobile terminals are smartphones or tablet PCs, which nowadays in almost all available models have a sensor screen (usually referred to as touchscreen), one or more cameras, acceleration sensors and other sensors such as gyroscope sensors and further components such as wireless interfaces for mobile radio or WLAN (Wireless LAN). The weight of such mobile terminals is typically less than 2 kg, usually less than 1 kg, and far less than that still. Computer programs for such mobile terminals are usually referred to as apps (short for the English word "application," i.e., application program).

In order to arrange, i.e., to center, spectacle lenses correctly in a spectacle frame, such that the spectacle lenses are worn in a correct position relative to the eyes of a person who is intended to wear spectacles, so-called centration parameters are used. Some of these centration parameters are defined for example in section 5 of the standard DIN EN ISO 13666: 2012 and comprise for example the pupillary distance PD in accordance with point 5.29 of this standard. Another of these centration parameters is the box height of the boxing system mentioned in 5.1 of this standard and defined in more specific detail in the standard DIN EN ISO 8624:2015.

Apparatuses and methods which enable such centration parameters to be determined automatically have been developed in recent years. In this regard, the Zeiss Visufit 1000 is a centration system which uses an inherently calibrated camera system in order to capture at least one eye area of a person's head, with a spectacle frame being worn, from a plurality of directions and to determine the centration parameters therefrom. This device is stationary and intended for application on the part of an optician.

Other procedures use a measuring brace which is attached to the spectacle frame and serves as a reference. Such procedures are known from U.S. Pat. No. 9,928,421 B1, 9,971,172 B1, 7,950,800 B1, 8,360,580 B1, or 9,535,270 B2.

In U.S. Pat. No. 9,928,421 B1, a person wearing spectacles and a measuring brace is recorded from different directions in that case. During the recordings, an inclination angle of the camera used for the respective recordings is ascertained such that an inclined arrangement of the camera can be taken into account. Centration parameters are then determined from the recordings.

U.S. Pat. No. 9,971,172 B1 discloses a centration device in which dimensions of a spectacle frame that are projected onto an image plane can be corrected in relation to a head posture in order to be able to determine centration data as accurately as possible even in the case of relatively large inclination angles of a camera used and rotation angles of the head. In that case, a single front image of the head is used, that is to say an image recording from the front, required inclination and rotation angles being determined from the imaging of a measuring brace.

U.S. Pat. No. 7,950,800 B1 discloses determining centration data, which once again involves using a measuring brace in order to offer a scale for recordings by a camera which records a front view of a person. An inclination of the camera is once again taken into account in that case.

U.S. Pat. No. 8,360,580 B1 describes how the so-called center of rotation of the eye can be determined with the aid of image capture by a camera and the use of marking elements on the head of a person. The position of the center of rotation of the eye is relevant in the calculation of centration parameters if the viewing direction adopted at the time of capture does not correspond to the so-called distance-vision viewing direction, where the person's gaze is directed essentially to infinity. In this document, the position of the center of rotation of the eye is determined with the aid of two captured recordings that image the person with different viewing directions. Markings on the head are used in order to be able to determine absolute sizes.

U.S. Pat. No. 7,950,800 B1 also describes methods for determining centration parameters by means of a handheld camera, with a measuring brace once again being used as an absolute size scale.

U.S. Pat. No. 9,535,270 B2 discloses a method in which a stationary video camera records a person while the person raises his/her head and pays attention to a stationary target in the process. In that case, a signal of an inclinometer selects, from the resultant series of image recordings during the raising of the head, that recording which best reproduces a normal head posture. In that case, the face is recorded by a front camera of a tablet PC. A measuring brace worn by the person is imaged by both cameras, that is to say the video camera and the front camera of the tablet PC. In that case, the two cameras form an angle of approximately 30°. Centration parameters are then determined from the image recordings.

The methods and apparatuses described above necessarily require a measuring brace (or other scale) or a multi-camera system and are intended, in principle, for implementation by an optician or another appropriately trained person. Both methods are suitable primarily for the field of stationary use, and only to a limited extent for mobile terminals.

U.S. 2018/140 186 A1 describes a method according to the preamble of claim 1. DE 10 2011 009 646 A1 describes a further method which uses a plurality of image recordings and the measurement of an acceleration.

SUMMARY

There is a need for simplified procedures for determining at least some centration parameters which can be implemented by means of a mobile terminal such as a smartphone or tablet PC and which can be implemented in particular by a person who is actually to be examined, without relatively high complexity. Proceeding from methods and apparatuses which use measuring braces, for example as in U.S. Pat. No. 7,950,800 B1, it is an aspect of the disclosure to provide methods and apparatuses in which such measuring braces or other aids are at least not absolutely necessary.

This object is achieved in accordance with a first aspect of the disclosure by means of a computer-implemented method and a corresponding mobile terminal taking into account image angle properties of the camera, the image angle properties specifying pixels of an image sensor of the camera, is achieved in accordance with a second aspect of the disclosure by means of a computer-implemented method and a corresponding mobile terminal, taking into account a rectilinear movement of the mobile terminal parallel to the optical axis of the camera toward the eye area or away from the eye area, is achieved in accordance with a third aspect of the disclosure by means of a computer-intimated method and a corresponding mobile terminal, taking into account a 3D model of the eye area, and is achieved in accordance with a fourth aspect of the disclosure by means of a computer-implemented method and a corresponding mobile terminal, taking into account that corneal vertex distance is determined as a difference between the distance between the camera and the pupil and the distance between the camera and the spectacle frame. Further exemplary embodiments and also a method for fitting spectacle lenses by grinding are disclosed below. Corresponding computer programs are additionally provided.

According to the disclosure, in all aspects, a computer-implemented method for a mobile terminal is provided, comprising:

capturing a first image of at least one eye area of a person by means of a camera of the mobile terminal at a first position of the mobile terminal, capturing a second image of the eye area of the person by means of the camera at a second position of the mobile terminal, and determining at least one centration parameter on the basis of the first image and the second image.

The method comprises repeated measurement of an acceleration of the mobile terminal during a movement of the mobile terminal from the first position to the second position. The at least one centration parameter is then additionally ascertained on the basis of the repeatedly measured acceleration.

The second image need not necessarily be captured after the first image. By way of example, a video sequence comprising a multiplicity of images, including the first image and the second image, can be captured, wherein one further image or a plurality of further images of the multiplicity of images can lie between the first image and the second image. Additionally or alternatively, one further image or a plurality of further images of the multiplicity of images can also precede the first image or succeed the second image. The method can also additionally use such further images and associated positions and accelerations for determining centration parameters.

The at least one centration parameter can comprise the pupillary distance. If the person is wearing a spectacle frame, the at least one centration parameter can additionally or alternatively comprise a height of the boxing system of the spectacle frame or other measures of the boxing system of the spectacle frame. In this regard, the pupillary distance or measures of the boxing system can be determined in a simple manner.

The eye area of a person is a part of the person's face which includes at least the person's eyes and, if the person is wearing a spectacle frame, a spectacle frame worn by the person. Here, pursuant to DIN ESO 7998:2006-01 and DIN ESO 8624:2015-12, a spectacle frame should be understood to mean a frame or a holder by means of which spectacle lenses can be worn on the head. In particular, the term as used herein also includes rimless spectacle frames. Colloquially, spectacle frames are also referred to as frames.

Such a method does not require an additional scale such as a measuring brace or measurement points on a head of the person. By means of repeated measurement of the acceleration, it is possible, by integrating the acceleration twice, to determine a path of the mobile terminal from the first position to the second position, in particular a distance between the first position and the second position. This then makes it possible to determine the at least one centration parameter without using a scale. In this case, repeated measurement is understood to mean measurement with a rate, i.e., a number of measurement values per unit time, such that the path of the mobile terminal can be determined sufficiently accurately in order to be able to determine the centration parameters accurately enough for the spectacle lens centration. In the case of customary mobile terminals, the acceleration measured by a built-in acceleration sensor of the mobile terminal is digitally processed with a sampling rate. A sampling rate of 10 Hz, i.e., 10 acquired measurement values per second, or even less than that, may be sufficient for the method according to the disclosure. In this case, the measurement values can be subjected to low-pass filtering in order to increase the accuracy. Higher sampling rates are likewise possible and can increase the accuracy. The sampling rate is upwardly limited by the speed of the hardware components of the mobile terminal. In this case, a continuous measurement can be approximated by high sampling rates.

A camera and a sensor for measuring the acceleration are present practically in every commercially available mobile terminal such as a smartphone or a tablet PC. Consequently, by means of simply providing a computer program for the mobile terminal, that is to say an app, it is possible for the above method to be implemented without additional hardware being required.

For the purpose of acquiring the at least one centration parameter, the position of the pupils in the first image and the second image and/or the spectacle frame in the first image and second image can be identified by means of conventional image processing methods. For the frame rim of a spectacle frame, such methods are described in EP 3 355 214 A1, for example. For the purpose of detecting the position of the pupils in the image, corresponding methods are described in S. Kim et al., "A Fast Center of Pupil Detection Algorithm for VOG-Based Eye Movement Tracking," Conf Proc IEEE Eng Med Biol Soc. 2005; 3:3188-91 or in Mansour Asadifard and Jamshid Shanbezadeh, "Automatic Adaptive Center of Pupil Detection Using Face Detection and CDF Analysis," Proceedings of the International MultiConference of Engineers and Computer Scientists 2010 Vol I, IMECS 2010, Mar. 17-19, 2010, Hong Kong.

In this aspect, preferably also in the other aspects, determining the at least one centration parameter is additionally effected on the basis of image angle properties of the camera. These image angle properties specify the pixels of an image sensor of the camera on which an object which is at a specific angle with respect to the optical axis of the camera is imaged. In other words, the image angle properties specify a correlation between this angle with respect to the optical axis and the pixel. In this case, the optical axis denotes at the camera an axis of symmetry of the optical system of the camera, which system is usually rotationally symmetrical.

Such image angle properties thus enable an assignment between pixels in which objects such as, for example, the pupils are captured and angles, which enables corresponding centration parameters to be calculated in a simple manner.

The image angle properties of the camera can be determined for example from manufacturer specifications regarding the image angle of a lens of the camera. However, in the first aspect, optionally also in other aspects, in the context of the computer-implemented method, the image angle properties are determined beforehand by a first determination image and a second determination image being captured by means of the camera, the mobile terminal being rotated between capturing the first determination image and the second determination image. In the first and second determination images, mutually corresponding objects (that is to say objects which are visible in both images) are then identified by means of image processing. The image angle properties can then be determined from the rotation, which can be measured by an orientation or acceleration sensor of the mobile terminal, and from the pixels on which the objects in the first and second determination images are imaged. By virtue of such a determination of the image angle properties, as in the first aspect, no specifications on the part of the manufacturer are needed.

For the purpose of carrying out the method, the mobile terminal can issue corresponding instructions to a person who is carrying out the method. This can be done for example via a loudspeaker of the mobile terminal or a display of the mobile terminal. By way of example, the person who is carrying out the method can be instructed to move the mobile terminal from the first position into the second position. It should be noted that the person who is carrying out the method can be identical with the person whose centration data are being determined, with the result that no optician is required. By virtue of the issuing of the instructions, even an untrained person can carry out the method.

The method can furthermore comprise measuring an orientation of the mobile terminal at the first position, at the second position and/or during the movement from the first position into the second position. Here the orientation indicates how the mobile terminal is oriented at the position at which it is situated in each case, and indicates an inclination of the mobile terminal, for example. The orientation can be specified for example by means of three angles with respect to the axis of a fixed coordinate system. The orientation of the mobile terminal then corresponds to the orientation of the camera of the mobile terminal. The combination of orientation and position is referred to sometimes, in particular in robotics, as pose, cf. DIN EN ISO 8373:2012.

In some exemplary embodiments, the determination of the at least one centration parameter can then additionally be performed on the basis of the orientation e.g., at the first position and/or second position. Effects resulting from the orientation can be compensated for as a result. By way of example, distances in the captured image may appear different depending on orientation, and such effects can be compensated for. This is based essentially on simple geometric considerations of how the eye area is imaged onto the image sensor of the camera depending on the orientation.

In an alternative exemplary embodiment, a message can be issued if the orientation of the mobile terminal deviates from a predefined orientation. This message can be a warning, combined with instructions to move the mobile terminal to the predefined orientation again. In this case, the predefined orientation is an orientation on which the determination of the at least one centration parameter is based, that is to say formulae and the like for the calculation of the at least one centration parameter proceed from this predefined orientation. The predefined orientation can be for example a vertical orientation of a display of the mobile terminal. In this case, different orientations do not have to be taken into account computationally, which simplifies the calculation, rather the person who is carrying out the method is urged to maintain the mobile terminal in the predefined orientation.

The movement can be a rectilinear movement toward or away from the eye area, such that the first position and the second position are captured at two different distances from the eye area. This is the case in the fourth aspect, optionally also in other aspects. The person who is carrying out the method can once again be given corresponding instructions for this purpose. This enables a relatively simple calculation, which is explained in greater detail later with reference to corresponding figures.

The movement can also be a movement substantially in a plane in front of the eye area, for example an arcuate movement. Here the centration parameters are then ascertained from the first image and the second image in the third aspect, optionally also in the first and second aspects, in a manner similar to triangulation (cf. The article "Triangulation (Messtechnik)" ["Triangulation (metrology)"] in the German-language Wikipedia, version on Apr. 13, 2018).

It should be noted that, over and above the use of the acceleration, a more extensive ascertainment of position and orientation of the mobile terminal, i.e., of the pose of the mobile terminal, is also possible, for example as described in S.-H. Jung and C. Taylor, "Camera trajectory estimation using inertial sensor measurements and structure from motion results," in Proceedings of the IEEE Computer Society, Conference on Computer Vision and Pattern Recognition, vol. 2, 2001, pp. II-732-II-737" and Gabriel Nützi, Stephan Weiss, Davide Scaramuzza, Roland Stiegwart, "Fusion of IMO and Vision for Absolute Scale Estimation in Monocular SLAM, available at the url doi.org/10.1007/s10846-010-9490-z". Sensor fusion techniques such as in "Sensor Fusion on Android Devices: A Revolution in Motion Processing (InvenSense, available at the url www.youtube.com/watch?v=C7JQ7Rpwn2k&feature=youtu.be)" can also be used.

In this case, a plurality of images comprising more than just the first image and the second image can also be captured during the movement. From such a plurality of images, in the second aspect, optionally also in the other aspects, a 3D model of the eye area or of the head is then created, in a similar manner to what is done in the device Visufit 1000 from Zeiss, cited in the introduction, on the basis of a plurality of camera images. From this 3D model of the head, optionally with a spectacle frame, centration parameters can then be ascertained as in the case of this stationary centration device.

A model, in particular a 3D model, should be understood to mean a three-dimensional representation of real objects, in this case the eye area, optionally with a spectacle frame, which are available as a data set in a storage medium, for example a memory of a computer or a data carrier. By way of example, such a three-dimensional representation can be a 3D mesh, consisting of a set of 3D points, which are also referred to as vertices, and connections between the points, which connections are also referred to as edges. In the simplest case, these connections form a triangle mesh. Such a representation as a 3D mesh describes only the surface of an object and not the volume. The mesh need not necessarily be closed.

In this case, the 3D model can be a simplified 3D model which specifies the position of the pupils and the position of the spectacle frame, the latter represented in accordance with the boxing system. In this case, the position of the pupils when looking straight ahead into the distance can be determined indirectly by way of the position of the mechanical center of rotation of the eye, as will also be explained later with reference to figures. In this case, according to the internet link www.spektrum.de/lexikon/optik/augendrehpunkt/264, the mechanical center of rotation of the eye is that point of the eye which changes its position the least during changes in the viewing direction, and—according to this source—lies on average 13.5 mm behind the anterior corneal vertex.

Techniques of simultaneous position determination and mapping that are known from robotics can be used for this purpose; see, for example, the Wikipedia article "simultaneous localization and mapping" in the German-language Wikipedia, version on Apr. 14, 2018, with the further references given there.

Moreover, generally by means of repeatedly capturing images with conventional procedures of error computation, it is possible to increase an accuracy by the plurality of images being treated as a plurality of measurements.

In the above exemplary embodiments, a plane of an image sensor of the camera and a plane of the spectacle frame are kept substantially parallel. A measurement of the "as-worn" pantoscopic angle (defined in DIN EN ISO 1366 6: 2012; page 18) is not possible in a practical and targeted manner. In some exemplary embodiments, the "as-worn" pantoscopic angle can be input, and can influence the determined 3D model. The same applies to the corneal vertex distance in accordance with DIN EN ISO 1366 6: 2012; page 27, which can likewise be input separately. In the fourth aspect, by contrast, the corneal vertex distance is determined by a first distance between the camera and the spectacle frame and a second distance between the camera and a pupil of the person being determined and the corneal vertex distance being determined as the difference between the second distance and the first distance. In this regard, the corneal vertex distance can be determined even in the case of a rectilinear movement of the camera.

In other exemplary embodiments, the "as-worn" pantoscopic angle can also be measured by the mobile terminal being moved for example in a hemisphere or other three-dimensional movements in front of the face of the eye area and a 3D model which takes account of the "as-worn" pantoscopic angle thus being able to be created. In this case, a three-dimensional movement is a movement which comprises components in three linearly independent spatial directions.

Even if the methods described above are implementable without a measuring brace or other scale, in some exemplary embodiments such a scale can be provided, which is to be fitted at the eye area of the person. In this case, a scale is a device whose size is known and which can therefore serve as a size reference in the first image or second image. However, the accuracy of the methods described can also be increased, particularly when creating a 3D model as described above.

In other exemplary embodiments, a dimension of a spectacle frame worn by the person can be provided by way of an input on the mobile terminal. Such a dimension can be the height or width of the spectacle frame in the boxing system. This can be specified by a manufacturer of the spectacle frame or be gauged manually. This likewise provides a scale for the first image and the second image by the spectacle frame in these images being identified as explained above and the dimension in the image being related to the dimension that is input. This, too, is optional, however, and other exemplary embodiments require neither an input of a dimension nor an external scale.

In accordance with a further exemplary embodiment, a mobile terminal is provided, comprising a processor, a camera and an acceleration sensor. In this case, the processor is programmed, for example by way of a computer program stored in a memory of the mobile terminal, to carry out one of the methods described above, that is to say to cause a first image of an eye area to be captured at a first position of the mobile terminal, a second image of the eye area to be captured at a second position of the mobile terminal and centration parameters to be determined on the basis of the first image and the second image. This involves repeated measurement of an acceleration of the mobile terminal during the movement from the first position into the second position, and the determination of the centration parameter is additionally based on the basis of the repeated measurement of the acceleration.

Finally, a computer program for a mobile terminal, that is to say an app, is also provided which, when it is executed on the mobile terminal, has the effect that one of the methods described above is carried out. This computer program can be stored on a nonvolatile data carrier such as a memory card, a hard disk, an optical data carrier such as a DVD or CD and the like or can be transmitted by way of a data carrier signal.

The centration parameters determined can then be used for fitting a spectacle lens by grinding in a manner known per se. Accordingly, a method for fitting a spectacle lens by grinding using the at least one centration parameter which is determined by one of the above methods is also provided.

BRIEF DESCRIPTION OF THE DRAWINGS

The disclosure will now be described with reference to the drawings wherein.

DESCRIPTION OF EXEMPLARY EMBODIMENTS

Figure 1:
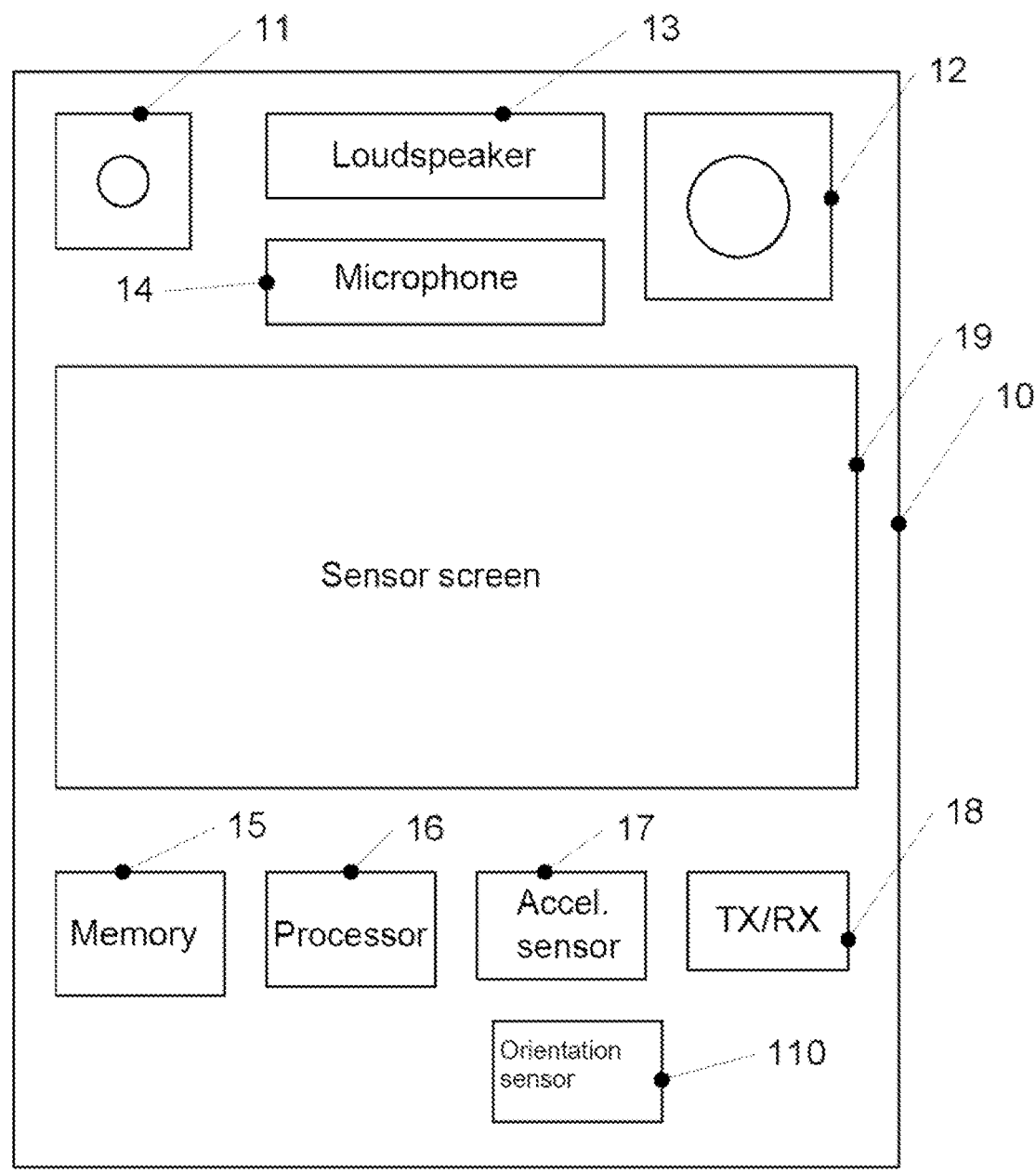
FIG. 1 shows a block diagram of a mobile terminal such as is used in exemplary embodiments.

The exemplary embodiments described below use a mobile terminal for determining the pupillary distance and also a height of the boxing system of a spectacle frame and optionally other centration parameters. FIG. 1 shows a block diagram of a mobile terminal 10 such as is used in such exemplary embodiments. The mobile terminal here can be a smartphone or a tablet computer. Smartphones or tablet computers available nowadays typically have at least the components illustrated in FIG. 1, but can also have further components.

The mobile terminal 10 in FIG. 1 has a sensor screen 19 (referred to as "touchscreen"), which serves as an input device and also for outputting for example instructions to a person. The mobile terminal 10 is controlled by a processor 16, which can access a memory 15, in which computer programs can be stored. As already mentioned in the introduction, such computer programs for mobile terminals are also referred to as apps. In the case of the mobile terminal 10, a computer program for carrying out one of the methods described below is stored in the memory 15.

The mobile terminal 10 furthermore has a loudspeaker 13 for outputting sounds, and a microphone 14. Via the loudspeaker 13, instructions can be output to a person who is carrying out the method, and voice commands, for example, can be received via the microphone 14.

The mobile terminal 10 furthermore has a front camera 11 and a rear camera 12. In this case, the front camera 11 is arranged on the same side as the sensor screen 19, such that a person, in particular the eye area of a person observing the sensor screen 19, can be captured by means of the front camera 11. The rear camera 12 is arranged on the opposite side of the mobile terminal 10 to the sensor screen 19.

Furthermore, the mobile terminal 10 has an acceleration sensor 17, by means of which accelerations of the mobile terminal 10 can be measured, and also an orientation sensor 110, by means of which an orientation of the mobile terminal 10 can be measured. Such an orientation sensor is sometimes also referred to as an inclination sensor. It should be noted that the acceleration sensor 17 and the orientation sensor 110 are illustrated as separate components in FIG. 1 in order to elucidate the different functions used in the context of the methods described below. However, the functions can also be provided by a common sensor device.

Finally, provision is made of a communication circuit 10 for transmitting (TX, from "transmitter") and receiving (RX, from "receiver") data, for example via a mobile radio network and/or via a WLAN network ("Wireless LAN"). Via these communication circuits, the centration data determined can be transmitted to an optician, for example, who then uses this data for fitting spectacle lenses by grinding.

Figure 2:
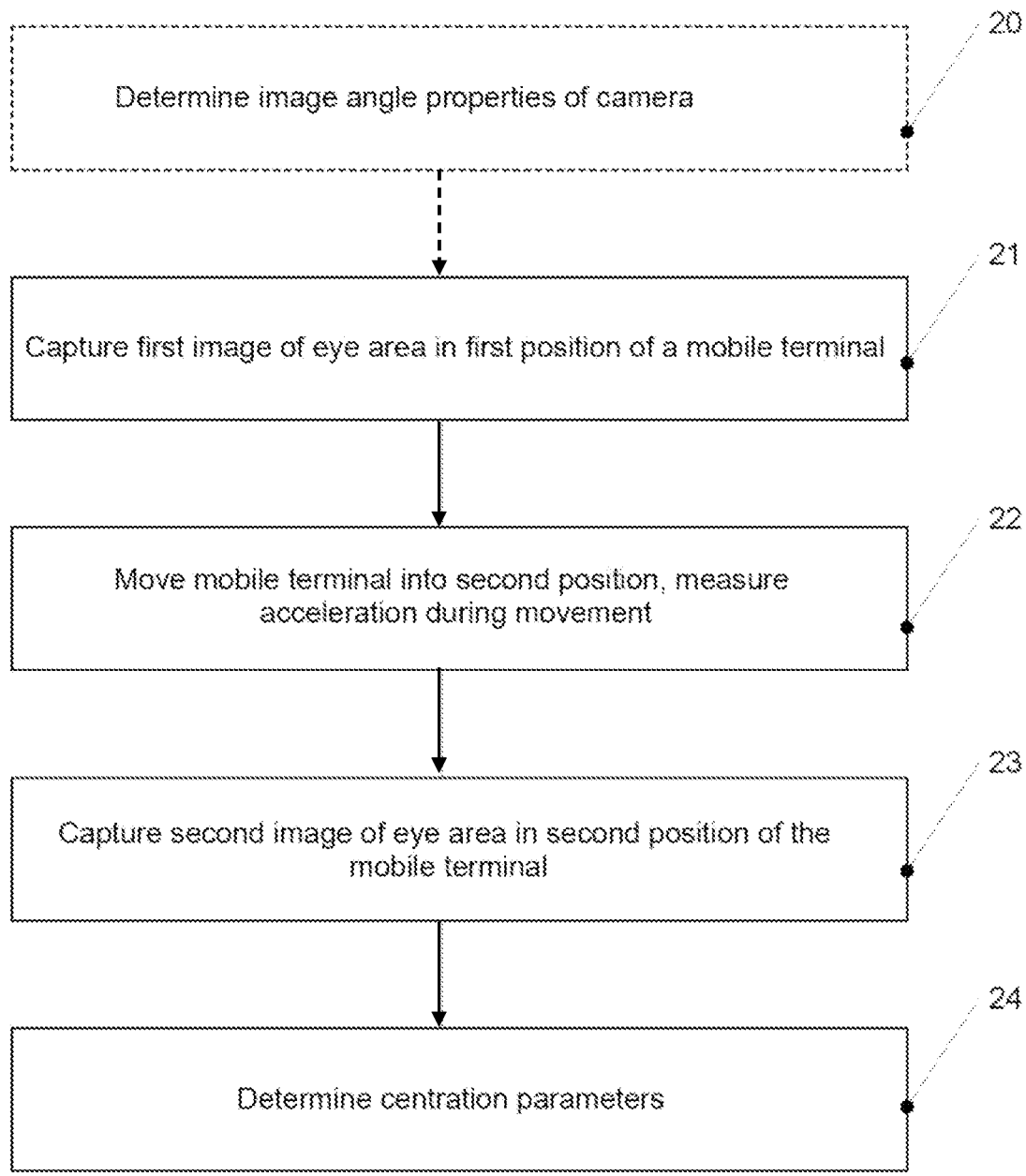
FIG. 2 shows a flow diagram of a method for determining at least one centration parameter in accordance with one exemplary embodiment.

FIG. 2 shows a flow diagram for elucidating a method in accordance with one exemplary embodiment, which is realized by corresponding programming of the processor 16 of the mobile terminal 10. For elucidating the steps of the method in FIG. 2, reference is made to FIGS. 3 to 7.

In step 20, the image angle properties of a camera used for the subsequent steps, i.e., of the front camera 11 or of the rear camera 12, of the mobile terminal, can optionally be determined. This determination need only be carried out once and is not carried out each time the following steps are carried out. As an alternative to optional step 20, the image angle properties can also be obtained in a different way. By way of example, the image angle properties can already be present as manufacturer specifications and then be input, or in some cases they can also be stored in the mobile terminal by the manufacturer and then be read out from the memory.

Figure 3:
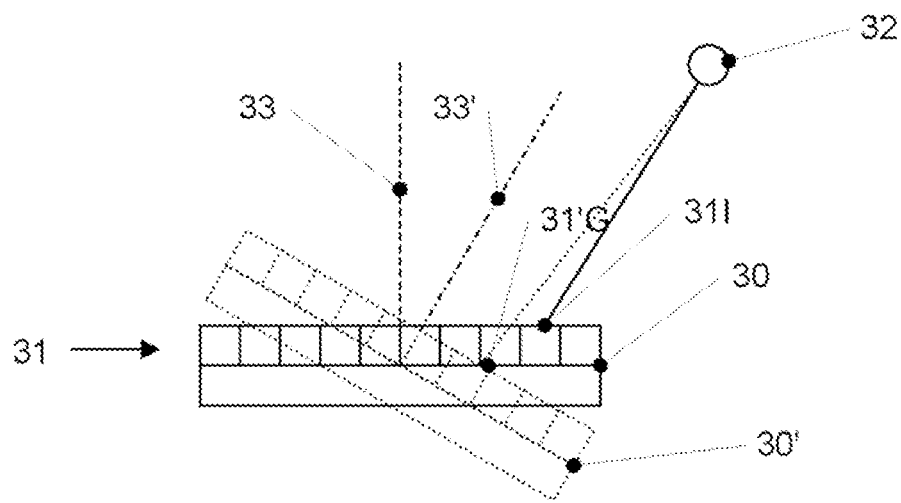
FIG. 3 shows a diagram for elucidating the determination of image angle properties of the camera.

One implementation of step 20 will be explained with reference to FIG. 3. In this case, FIG. 3 shows an image sensor 30 of the camera 11 or 12, which sensor has a multiplicity of pixels 31, in a cross-sectional view. For elucidation purposes, ten pixels 31 are illustrated, which from left to right are designated by A to J (that is to say 31A to 31J). In this case, resolutions of typical cameras of mobile terminals are in the range of several megapixels, and so the illustration in FIG. 3 is simplified in order to be able to better elucidate the procedure.

Firstly, an image with a plurality of objects is captured in a first orientation of the image sensor 30. One object 32 is illustrated here as an example. The captured objects such as the object 32 are preferably situated at a relatively large distance from the image sensor 30, for example >1 m, >5 m or >10 m, in order to minimize errors owing to camera movements. In the simplified example in FIG. 3, the object 32 is imaged onto the pixel 31I by an optical unit (not illustrated). The optical axis of the camera is designated by 33.

The camera is then rotated about an axis perpendicular to the image plane in FIG. 3. The image sensor 30 in this new position is designated by 30'. In this rotated position, the object is now at a different angle with respect to the optical axis 33 (designated by 33' for the position 30'), and the object 32 is now imaged onto the pixel 31'G. The object 32 can be recognized in both captured images by means of the image analysis methods already mentioned. This can be done for a multiplicity of such objects 32. From the displacements of the objects between the two images, i.e., the changes regarding the pixels onto which the objects are imaged, the image angle properties of the camera can then be determined. In this case, the angle by which the camera is rotated is measured by means of the orientation sensor 110. The rotation illustrated can be effected twice in this case, namely—as regards the rotation illustrated in FIG. 3—about an axis perpendicular to the image plane and about an axis that is perpendicular thereto and is likewise parallel to a surface of the image sensor 30. The image angle properties can thus be ascertained in two mutually perpendicular directions and thus for an entire—usually— rectangular image sensor in step 20. In this case, the determination of the image angle properties can be adversely affected by distortions such as pincushion or barrel distortion during image capture. However, mobile terminals here usually have an intrinsic calibration which at least substantially eliminates such distortions computationally.

In order to prevent unwanted translations of the camera and thus of the image sensor 30 during the rotation of the camera from corrupting the result, a translation of the camera that is possibly superposed on the rotation of the camera can be detected and computationally separated from the rotation in order thus to compensate for an influence of the translation. Measurement values of the acceleration sensor 17 of the mobile terminal and/or the captured images can be used for this purpose. This compensation is facilitated if the captured objects such as the object 32 are situated at different distances from the camera in the image field thereof. In this case, the calculation of the translation according to a position change can be effected as in the references Jung et al. or Mitzi et al., cited above.

In step 21 in FIG. 2, a first image of an eye area is captured in a first position of the mobile terminal. In step 22, the mobile terminal is then moved into a second position, the acceleration during the movement from the first position to the second position being measured. In step 23, a second image of the eye area is then captured in a second position of the mobile terminal.

Figure 4:
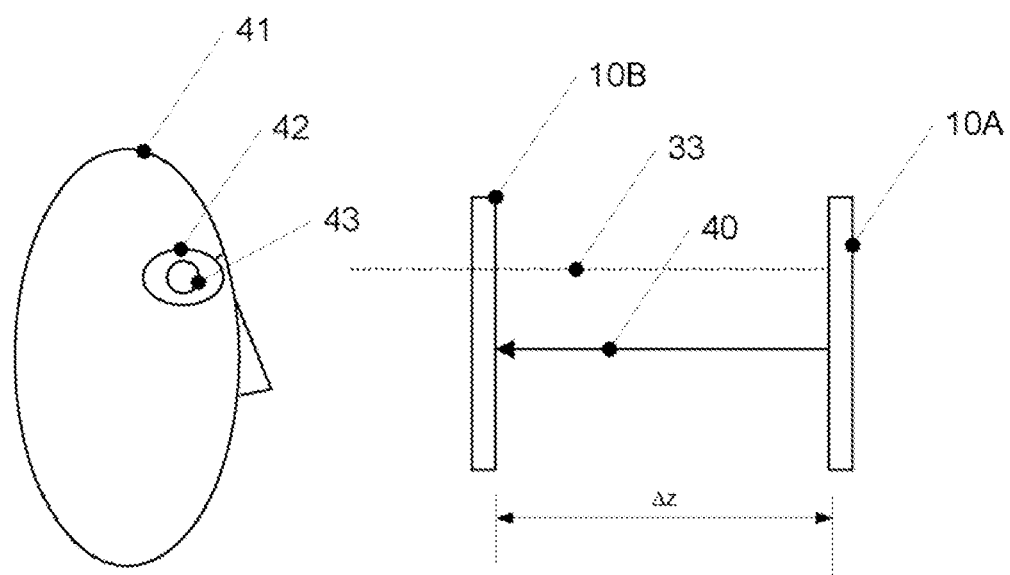
FIG. 4 shows a diagram for elucidating one possible implementation of steps 21 to 23 from FIG. 2.

One possible implementation of these steps 21-23 is elucidated in FIG. 4. In the case of the implementation in FIG. 4, firstly an image of an eye area of a person 41, of whom a head is illustrated, is captured in a first position of the mobile terminal 10, designated by 10A in FIG. 4. The reference sign 43 designates the right eye of the person, who in this case is wearing a spectacle frame 42. If the person 41 is carrying out the method, the image capture is expediently effected by means of the front camera 11 of the mobile terminal in order that the person can observe the sensor screen 19 and instructions and indications given thereon at the same time as the movement. If the method is carried out by some other person, for example an optician, the image capture is expediently effected by means of the rear camera 12, such that the other person can then observe the sensor screen 19. In the case of the implementation in FIG. 4, here the mobile terminal is held such that the optical axis 33 is directed at the head 41, in particular approximately at the eye area. This alignment can be checked by means of the orientation sensor 110, and for example in the case of an orientation of the mobile terminal 10 from the position illustrated in FIG. 4, an indication to correctly align the mobile terminal 10 again can be issued to the person who is carrying out the method.

The mobile terminal 10, as indicated by an arrow 40, is then moved parallel to the direction of the optical axis 33 toward the head 41 into a second position designated by 10B, and the second image is captured here. The correct direction of the movement can once again be checked by means of the sensors of the mobile terminal 10 and, if appropriate, an indication can be issued to the person who is carrying out the method. During the movement, the acceleration of the mobile terminal 10 is measured by means of the acceleration sensor 17. A distance between the first position and the second position is designated by $\Delta z$ in FIG. 4. In this case, the camera is kept approximately at the level of the pupils, and the eyes 43 look at the camera. In this way, the optical axis of the camera matches the person's viewing direction.

In the case of the implementation in FIG. 4, image capture can also be effected repeatedly during the movement in order to increase the accuracy.

In step 24, centration parameters are then determined from the first image, the second image and the measured acceleration using the image angle properties of the camera. For the implementation in FIG. 4, this will now be explained with reference to FIGS. 5A to 5C and also 6.

In order to determine centration parameters, firstly the distance $\Delta z$ between the first position and the second position is ascertained on the basis of the measured acceleration. For the implementation in FIG. 4, this will be explained with reference to FIGS. 5A to 5C.

Figure 5A:
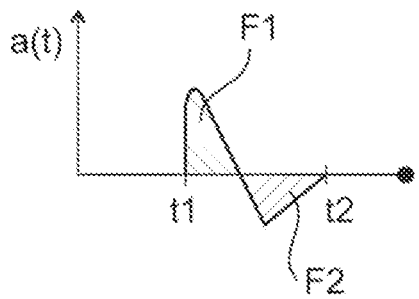
FIGS. 5A to 5C show diagrams for elucidating the determination of a distance $\Delta z$ from FIG. 4 on the basis of acceleration data.

FIG. 5A shows one example of the acceleration a(t) over time t for the movement from the first position 10A to the second position 10B in FIG. 4. In this case, the duration of the movement is from a time t1 to a time t2. The acceleration is firstly positive when the mobile terminal 10 is accelerated from the first position 10A, and then negative when the mobile terminal 10 is decelerated again in order to come to rest at the second position 10B. The region in which the acceleration is positive is designated by F1, and the region in which the acceleration is negative is designated by F2.

Figure 5B:
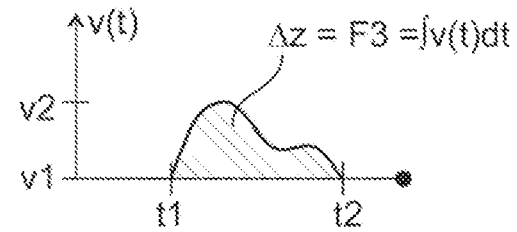
Figure 5C:
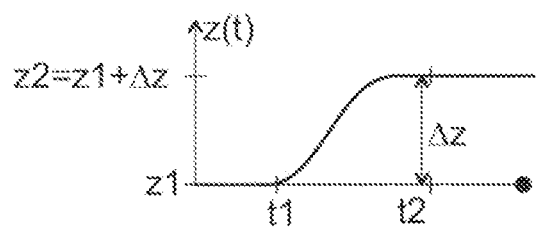

Integration of the acceleration yields the velocity, as is shown in FIG. 5B. The mobile terminal is at rest at the beginning of the movement (v1) and at the end of the movement (v2), such that the integration constant for determining the velocity can be set to zero. The area F3, that is to say the integral of the velocity over time, then yields the desired distance $\Delta z$, as is illustrated in FIG. 5C. The z-position in the position 10A, designated by z1 in FIG. 5C, can be assumed to be 0 in this case, since only the value $\Delta z$ is of interest for the subsequent determination and the absolute position is not required.

Figure 6:
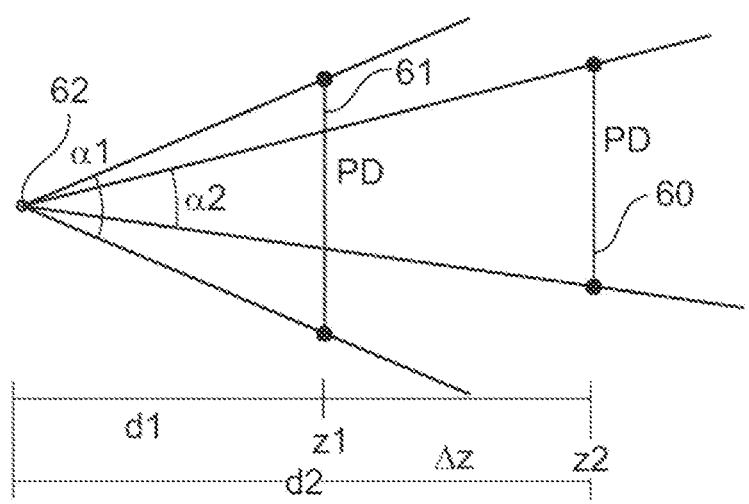
FIG. 6 shows a diagram for elucidating the determination of a pupillary distance in the implementation from FIG. 4.

The calculation of centration parameters will be explained on the basis of the example of the pupillary distance with reference to FIG. 6. In this case, the pupillary distance such as appears at the first position 10A in the first image is designated by 60, and the pupillary distance in the second image such as appears at the second position 10B is designated by 61. The respective position of the mobile terminal is designated by 62. In FIG. 6, therefore, in order to elucidate the geometric relationships, the position of the mobile terminal is fixedly designated by 62, and the different distances with respect to the head 41 are illustrated by different distances of the pupillary distance 60 and 61, respectively, from this point 62.

The distance between the mobile terminal at the first position 10A and the head 41 is designated by D2, and the distance at the second position 10B with respect to the head 41 is designated by D1. On the basis of the image angle properties discussed above, from the positions of the pupils in the first image and the second image, that is to say from the pixels on which the pupils appear in the first image and in the second image, it is possible to determine an angle $\alpha 2$ for the first image and an angle $\alpha 1$ for the second image at which the pupillary distance appears as viewed from the camera, as is identified in FIG. 6.

From the values $\alpha 1$, $\alpha 2$ and $\Delta z$ determined above, it is possible to calculate the pupillary distance PD as follows:

$$\tan(\alpha 2/2) = \frac{PD/2}{d2} = \frac{PD/2}{d1 + \Delta z}$$

$$\tan(\alpha 1/2) = \frac{PD/2}{d1}$$

$$\frac{1}{\tan(\alpha 2/2)} - \frac{d1 + \Delta z}{\frac{PD}{2}} = \frac{1}{\tan(\alpha 1/2)} - \frac{d1}{PD/2}$$

$$\left(\frac{1}{\tan(\alpha 2/2)} - \frac{1}{\tan(\alpha 1/2)}\right)^{-1} * \Delta z * 2 = PD$$

Other geometric variables from the first image and the second image, such as the height of the spectacle frame in the boxing system or the width, can be calculated in the same way. In this case, in the equations above, PD is then replaced by the corresponding geometric variable. In this way, centration parameters can be determined as dimensions in the first and second images in a simple manner.

Additionally, after the calculation of PD, from the equations above, the values d1, d2 can also be calculated. Consequently, the distance between the camera of the mobile terminal and the pupils is then known. The same can be carried out for the spectacle frame. From the difference between the camera-pupil distance and the camera-spectacle frame distance, the corneal vertex distance as a further centration parameter can additionally be calculated as the difference between the two distances.

Alternatively, a fixed value for the corneal vertex distance can also be assumed, or the latter can be input from other sources.

Figure 7:
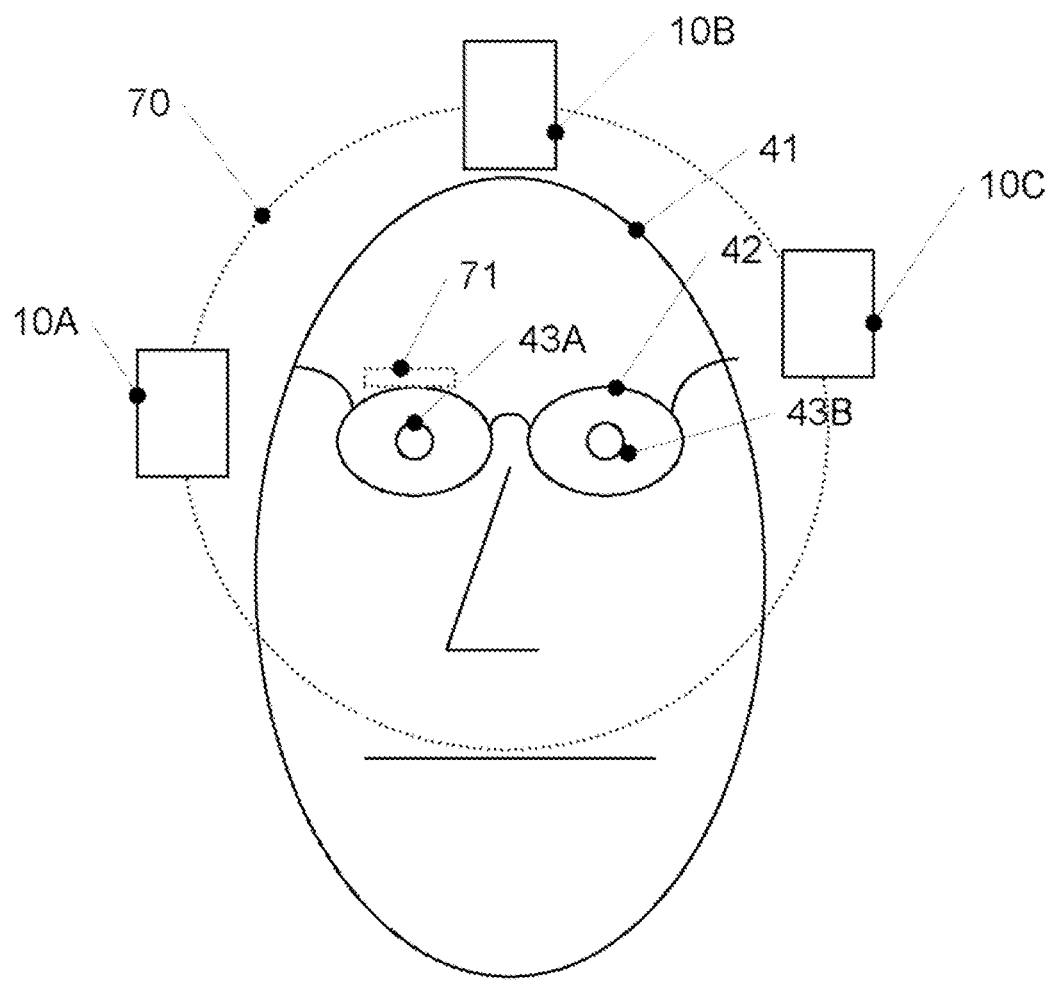
FIG. 7 shows a diagram for elucidating a further possible implementation of steps 21 to 23 of the method from FIG. 2.

FIG. 7 shows an alternative implementation for steps 21 to 23 from FIG. 2. Here the mobile terminal is moved in a plane in front of the eye area of the head 41, and images of the eye area are captured in at least two positions. Three positions 10A, 10B, 10C along a circular path 70 are shown as an example in FIG. 7. The relative pose of the positions can be determined by measuring the three-dimensional acceleration during the movement between the positions. In this case, a circular path as in FIG. 7 need not be present, rather it is also possible to use some other path, for example some other arcuate path.

The centration data, such as the pupillary distance, can then be determined in step 24 essentially as in the case of a triangulation, as has already been explained in the introduction. The orientation of the mobile terminal, that is to say the orientation in each of the positions in which an image is captured, can also be used for this purpose.

The captured recordings in FIG. 7 can be used to create a simplified 3D model comprising the spectacle frame, represented by the measures in the boxing system, and the eyes (represented by the pupils, or by the centers of rotation of the eyes). In this case, the person looks continuously in a defined direction, e.g., directly into the camera or at a known, fixed point in the distance. The positions of the centers of rotation of the eyes or the positions of the pupils can be determined in this way. If this is the case, the positions of the centers of rotation of the eyes and therefrom the positions of the pupils and hence the pupillary distance or directly the positions of the pupils of both eyes can thus be determined. These two possibilities will now be explained with reference to FIGS. 8A and 8B.

Figure 8A:
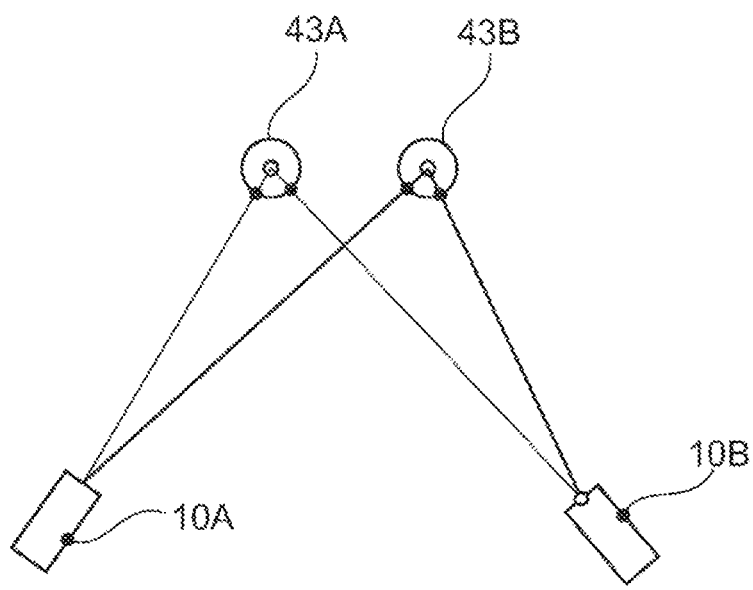
FIGS. 8A and 8B show diagrams for elucidating the determination of a position of the center of rotation of the eye or of the pupil.

FIG. 8A shows a case in which the person is looking at the mobile terminal 10, which is illustrated in two positions 10A, 10B. The pupils of the eyes 43A, 43B are illustrated as black dots and in this case follow the position of the mobile terminal 10, that is to say that they are directed at the mobile terminal 10 in the respective position 10A or 10B. If a triangulation as mentioned above is then carried out on the basis of the pose of the pupils in the images respectively captured in the positions 10A, 10B, the result produced is the positions of the centers of rotation of the eyes, as evident from FIG. 8A, according to the intersection points of the connecting lines from the positions 10A, 10B to the respective positions of the pupils. From these, the position of the pupils when looking straight ahead into the distance can then be estimated by adding a value of approximately 13.5 mm as average distance of the center of rotation of the eye from the anterior corneal vertex from the position of the centers of rotation of the eyes in the frontal direction of the person. The pupillary distance can in turn be determined from the positions of the pupils estimated in this way.

Figure 8B:
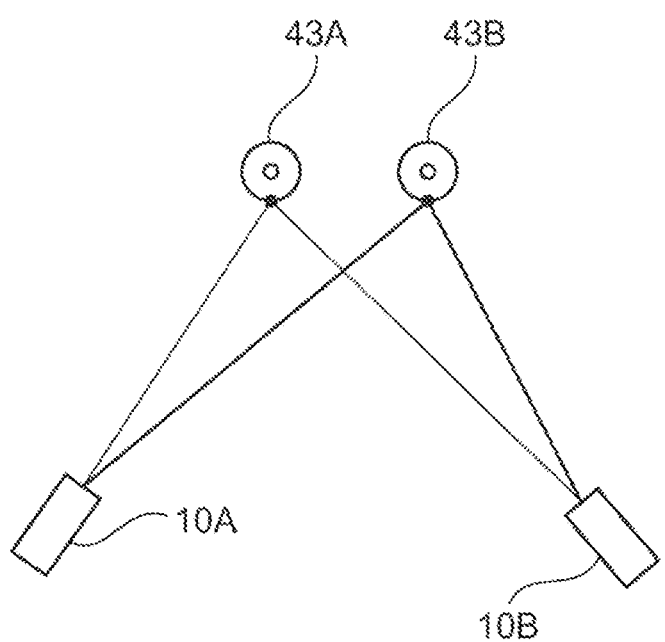

FIG. 8B illustrates the case in which the person is looking straight ahead at a target in the distance, while the mobile terminal captures images in the positions 10A, 10B. In this case, the pupils do not follow the mobile terminal 10, and the position of the pupils is determined directly by triangulation.

Further details concerning such position calculations on the basis of captured image recordings can also be gathered from U.S. 2013/083976 A, U.S. 2013/076884 A or WO 2015/101737 A1.

The image capture can also be effected repeatedly both in the case of FIG. 3 and in the case of FIG. 7, and in accordance with a plurality of images it is then possible to increase the accuracy of the determination of the centration parameters in accordance with a conventional error computation. In the case of the procedure in FIG. 7, a 3D model can be created, in particular.

As already mentioned in the introduction, the methods do not require a measuring brace or other scale. Optionally, such a scale, designated by the reference sign 71 in FIG. 7, can additionally be provided as a size scale in order to increase the accuracy of the determination. In particular, this can support the creation of the 3D model in the case of FIG. 7.

Some exemplary embodiments are defined by the following clauses:

Clause 1. A computer-implemented method for a mobile terminal for determining at least one centration parameter, comprising:
capturing a first image of an eye area of a person at a first position of the mobile terminal by means of a camera of the mobile terminal,
capturing a second image of the eye area at a second position of the mobile terminal by means of the camera, and
determining the at least one centration parameter on the basis of the first image and the second image,
characterized by
repeated measurement of an acceleration of the mobile terminal during a movement of the mobile terminal from the first position to the second position,
determining the at least one centration parameter additionally being effected on the basis of the repeated measurement of the acceleration.

Clause 2. The method according to clause 1, characterized in that determining the at least one centration parameter is additionally effected on the basis of image angle properties of the camera.

Clause 3. The method according to clause 2, characterized in that the method additionally comprises determining the image angle properties of the camera.

Clause 4. The method according to any of clauses 1 to 3, characterized by instructions for moving the mobile terminal from the first position to the second position being issued to a person by the mobile terminal.

Clause 5. The method according to any of clauses 1 to 4, characterized by:
measuring an orientation of the mobile terminal,
determining the centration parameter additionally being based on the orientation of the mobile terminal.

Clause 6. The method according to any of clauses 1 to 4, characterized by:
measuring an orientation of the mobile terminal, and
outputting an indication if the orientation differs from a predefined orientation.

Clause 7. The method according to any of clauses 1 to 6, characterized in that the movement comprises a rectilinear movement toward the eye area or away from the eye area.

Clause 8. The method according to any of clauses 1 to 7, characterized in that the movement comprises a movement in a plane in front of the eye area.

Clause 9. The method according to any of clauses 1 to 8, characterized in that the movement comprises a three-dimensional movement in front of the eye area.

Clause 10. The method according to any of clauses 1 to 9, characterized in that the at least one centration parameter comprises at least one parameter from the group comprising a pupillary distance, a measure of a boxing system, a corneal vertex distance and an "as-worn" pantoscopic angle.

Clause 11. The method according to any of clauses 1 to 10, characterized in that the method comprises capturing a multiplicity of images during the movement comprising the first image and the second image, determining the centration parameter being effected on the basis of the multiplicity of images.

Clause 12. The method as claimed in any of claims 1 to 11, characterized in that the method comprises creating a 3D model on the basis of the first image and the second image.

Clause 13. The method according to any of clauses 1 to 12, characterized in that the method does not use a scale to be fitted on the person.

Clause 14. The method according to any of clauses 1 to 13, characterized in that at least one capturing from the group comprising capturing the first image and capturing the second image comprises capturing a scale, determining the at least one centration parameter additionally being effected on the basis of the scale.

Clause 15. The method according to any of clauses 1 to 14, characterized in that the method furthermore comprises receiving a dimension of a spectacle frame worn by the person, a ratio of the dimension to a corresponding dimension in at least one image from the group comprising the first image and the second image serving as size scale.

Clause 16. A method for fitting a spectacle lens by grinding, comprising:
determining at least one centration parameter by means of the method according to any of clauses 1 to 15, and
fitting the spectacle lens by grinding on the basis of the at least one centration parameter.

Clause 17. A computer program for a mobile terminal comprising a program code which, when it is executed on a processor of the mobile terminal, has the effect that the mobile terminal carries out the method according to any of clauses 1 to 15.

Clause 18. A mobile terminal for determining at least one centration parameter, comprising:
a processor, a camera and an acceleration sensor, the processor being configured for:
capturing a first image of an eye area of a person at a first position of the mobile terminal by means of a camera of the mobile terminal,
capturing a second image of the eye area at a second position of the mobile terminal by means of the camera, and
determining the at least one centration parameter on the basis of the first image and the second image,
characterized in that the processor is furthermore configured for:
repeated measurement of an acceleration of the mobile terminal during a movement of the mobile terminal from the first position to the second position,
determining the at least one centration parameter additionally being effected on the basis of the repeated measurement of the acceleration.

Clause 19. The mobile terminal according to clause 18, characterized in that determining the at least one centration parameter is additionally effected on the basis of image angle properties of the camera.

Clause 20. The mobile terminal according to clause 19, characterized in that the processor is furthermore configured for determining the image angle properties of the camera.

Clause 21. The mobile terminal according to any of clauses 18 to 20, characterized in that the processor is furthermore configured for issuing instructions for moving the mobile terminal from the first position to the second position to a person by means of the mobile terminal.

Clause 22. The mobile terminal according to any of clauses 18 to 21, characterized in that the processor is furthermore configured for measuring an orientation of the mobile terminal,
determining the centration parameter additionally being based on the orientation of the mobile terminal.

Clause 23. The mobile terminal according to any of clauses 18 to 22, characterized in that the processor is furthermore configured for measuring an orientation of the mobile terminal, and
outputting an indication if the orientation differs from a predefined orientation.

Clause 24. The mobile terminal according to any of clauses 18 to 23, characterized in that the at least one centration parameter comprises a pupillary distance, a measure of a boxing system, a corneal vertex distance and/or an "as-worn" pantoscopic angle.

Clause 25. The mobile terminal according to any of clauses 18 to 24, characterized in that the processor is furthermore configured for capturing a multiplicity of images during the movement comprising the first image and the second image, determining the centration parameter being effected on the basis of the multiplicity of images.

Clause 26. The mobile terminal according to any of clauses 18 to 25, characterized in that the processor is furthermore configured for creating a 3D model on the basis of the first image and the second image.

Clause 27. A computer-readable nonvolatile data carrier comprising instructions which, when they are executed on a mobile terminal comprising a camera and an acceleration sensor, have the effect that the mobile terminal carries out the following steps:
capturing a first image of an eye area of a person at a first position of the mobile terminal by means of a camera of the mobile terminal,
capturing a second image of the eye area at a second position of the mobile terminal by means of the camera, and
determining the at least one centration parameter on the basis of the first image and the second image,
characterized by
repeated measurement of an acceleration of the mobile terminal during a movement of the mobile terminal from the first position to the second position,
determining the at least one centration parameter additionally being effected on the basis of the repeated measurement of the acceleration.

Clause 28. A data carrier signal which transmits a computer program which, when it is executed on a mobile terminal comprising a camera and an acceleration sensor, has the effect that the mobile terminal carries out the following steps:
capturing a first image of an eye area of a person at a first position of the mobile terminal by means of a camera of the mobile terminal,
capturing a second image of the eye area at a second position of the mobile terminal by means of the camera, and
determining the at least one centration parameter on the basis of the first image and the second image,
characterized by
repeated measurement of an acceleration of the mobile terminal during a movement of the mobile terminal from the first position to the second position,
determining the at least one centration parameter additionally being effected on the basis of the repeated measurement of the acceleration.

Clause 29. A mobile terminal comprising a processor, a camera, an acceleration sensor and a memory with a computer program stored therein, the processor being configured to control the mobile terminal, on the basis of the computer program, for carrying out the following steps:
capturing a first image of an eye area of a person at a first position of the mobile terminal by means of a camera of the mobile terminal, capturing a second image of the eye area at a second position of the mobile terminal by means of the camera, and
determining the at least one centration parameter on the basis of the first image and the second image,
characterized by
repeated measurement of an acceleration of the mobile terminal during a movement of the mobile terminal from the first position to the second position,
determining the at least one centration parameter additionally being effected on the basis of the repeated measurement of the acceleration.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer-implemented method for determining at least one centration parameter with a mobile terminal, the at least one centration parameter enabling spectacle lenses to be arranged correctly in a spectacle frame, the method comprising:
    capturing a first image of an eye area of a person at a first position of the mobile terminal with a camera of the mobile terminal,
    the mobile terminal having an intrinsic calibration for at least substantially eliminating distortions of the camera computationally;
    capturing a second image of the eye area at a second position of the mobile terminal with the camera; and
    determining the at least one centration parameter on a basis of the first image and the second image, and on a basis of image angle properties of the camera, the image angle properties specifying pixels of an image sensor of the camera on which an object which is at a specific angle with respect to the optical axis of the camera is imaged;
    repeated measurement of an acceleration of the mobile terminal during a movement of the mobile terminal from the first position to the second position being effected;
    determining the at least one centration parameter additionally being effected on the basis of the repeated measurement of the acceleration,
    wherein the method additionally comprises determining the image angle properties of the camera, and
    wherein, for a purpose of determining the image angle properties, same objects which are at a distance of more than one meter from the image sensor are captured with in each case two different angular positions of the mobile terminal for a rotation about a first axis parallel to the surface of the image sensor and about a second axis perpendicular to the first axis and parallel to the surface of the image sensor in a first determination image and a second determination image, and the image angle properties are determined from image position displacements of the objects between the respective first and second determination images for the first axis and the second axis and a respective rotation of the mobile terminal between the two different angular positions.

2. The method as claimed in claim 1, wherein the method comprises:
    creating a 3D model of the eye area on the basis of the first image and the second image; and
    determining the at least one centration parameter additionally being effected on the basis of the 3D model of the eye area.

3. The method as claimed in claim 1, wherein the movement comprises a rectilinear movement toward the eye area or away from the eye area.

4. The method as claimed in claim 1, wherein the movement comprises a movement selected from the group including a movement in a plane in front of the eye area and a three-dimensional movement in front of the eye area.

5. The method as claimed in claim 1, wherein the at least one centration parameter comprises at least one parameter from the group including a pupillary distance, a measure of a boxing system of a spectacle frame worn by the person, a corneal vertex distance, the person wearing a spectacle frame when the first image and the second image are captured, and an "as-worn" pantoscopic angle of a spectacle frame worn by the person.

6. The method as claimed in claim 1, wherein at least one capturing from the group including capturing the first image and capturing the second image comprises capturing a scale, and determining the at least one centration parameter additionally being effected on the basis of the scale.

7. The method as claimed in claim 1, wherein the method furthermore comprises receiving a dimension of a spectacle frame worn by the person, a ratio of the dimension to a corresponding dimension in at least one image from the group including the first image and the second image serving as size scale.

8. The method as claimed in claim 1, wherein:
    measuring an orientation of the mobile terminal, and
    determining the centration parameter additionally being based on the orientation of the mobile terminal.

9. The method as claimed in claim 1, further comprising:
    measuring an orientation of the mobile terminal, and
    outputting an indication if the orientation differs from a predefined orientation.

10. The method as claimed in claim 1, wherein the method comprises capturing a multiplicity of images during the movement, the multiplicity of images including the first image and the second image, and determining the centration parameter being effected on the basis of the multiplicity of images.

11. A method for fitting a spectacle lens by grinding, comprising:
    determining at least one centration parameter by means of the method as claimed in claim 1; and
    fitting the spectacle lens by grinding on the basis of the at least one centration parameter.

12. A computer program stored on a non-transitory storage medium for a mobile terminal, which has a processor, a camera, and an acceleration sensor, the computer program comprising a program code which, when it is executed on a processor of the mobile terminal, has the effect that the mobile terminal carries out the method as claimed in claim 1.

13. A computer-implemented method for determining at least one centration parameter with a mobile terminal, the at least one centration parameter enabling spectacle lenses to be arranged correctly in a spectacle frame, the method comprising:
   capturing a first image of an eye area of a person at a first position of the mobile terminal with a camera of the mobile terminal;
   capturing a second image of the eye area at a second position of the mobile terminal with the camera; and
   determining the at least one centration parameter on a basis of the first image and the second image;
   repeated measurement of an acceleration of the mobile terminal during a movement of the mobile terminal from the first position to the second position being effected;
   determining the at least one centration parameter additionally being effected on the basis of the repeated measurement of the acceleration,
   the movement including a rectilinear movement parallel to the optical axis of the camera toward the eye area or away from the eye area,
   the at least one centration parameter including a corneal vertex distance, the person wearing a spectacle frame when the first image and the second image are captured, and
   in each case at least the pupils of the person and the spectacle frame being imaged in the first image and in the second image,
   wherein a distance between the first position and the second position is ascertained on the basis of the repeated measurement of the acceleration;
   wherein a first distance between the camera and the spectacle frame and a second distance between the camera and a pupil of the person are determined on the basis of the ascertained distance and on the basis of image angle properties of the camera, the image angle properties specifying the pixels of an image sensor of the camera on which an object which is at a specific angle with respect to the optical axis of the camera is imaged, and
   wherein the corneal vertex distance is determined as a difference between the second distance and the first distance.

14. The method as claimed in claim 13, wherein the method additionally comprises determining the image angle properties of the camera.

15. The method as claimed in claim 13, wherein the at least one centration parameter additionally comprises at least one parameter from the group including a pupillary distance, a measure of a boxing system of a spectacle frame worn by the person,
   and an "as-worn" pantoscopic angle of a spectacle frame worn by the person.

16. A mobile terminal for determining at least one centration parameter, the mobile terminal comprising:
   a processor;
   a camera; and
   an acceleration sensor, the mobile terminal having an intrinsic calibration for at least substantially eliminating distortions of the camera computationally, and the processor being configured for:
   capturing a first image of an eye area of a person at a first position of the mobile terminal with a camera of the mobile terminal;
   capturing a second image of the eye area at a second position of the mobile terminal with the camera; and
   determining the at least one centration parameter on a basis of the first image and the second image, and on a basis of image angle properties of the camera, the image angle properties specifying the pixels of an image sensor of the camera on which an object which is at a specific angle with respect to the optical axis of the camera is imaged,
   the processor furthermore being configured for:
   repeated measurement of an acceleration of the mobile terminal during a movement of the mobile terminal from the first position to the second position; and
   determining the at least one centration parameter additionally being effected on the basis of the repeated measurement of the acceleration,
   wherein the processor is additionally configured for determining the image angle properties of the camera such that, for a purpose of determining the image angle properties, same objects which are at a distance of more than one meter from the image sensor are captured with in each case two different angular positions of the mobile terminal for a rotation about a first axis parallel to the surface of the image sensor and about a second axis perpendicular to the first axis and parallel to the surface of the image sensor in a first determination image and a second determination image, and the image angle properties are determined from image position displacements of the objects between the respective first and second determination images for the first axis and the second axis and a respective rotation of the mobile terminal between the two different angular positions.

17. A mobile terminal for determining at least one centration parameter, comprising:
   a processor;
   a camera; and
   an acceleration sensor, the processor being configured for:
   capturing a first image of an eye area of a person at a first position of the mobile terminal with a camera of the mobile terminal;
   capturing a second image of the eye area at a second position of the mobile terminal with the camera; and
   determining the at least one centration parameter on the basis of the first image and the second image,
   the processor furthermore being configured for:
   repeated measurement of an acceleration of the mobile terminal during a movement of the mobile terminal from the first position to the second position;
   determining the at least one centration parameter additionally being effected on the basis of the repeated measurement of the acceleration,
   the movement including a rectilinear movement parallel to an optical axis of the camera toward the eye area or away from the eye area,
   the at least one centration parameter including a corneal vertex distance, the person wearing a spectacle frame when the first image and the second image are captured, and
   in each case at least the pupils of the person and the spectacle frame being imaged in the first image and in the second image,
      wherein the processor is configured to ascertain a distance between the first position and the second position on the basis of the repeated measurement of the acceleration, to determine a first distance between the camera and the spectacle frame and a second distance between the camera and a pupil of the person on the basis of the ascertained distance and on the basis of image angle properties of the camera, the image angle properties specifying the pixels of an image sensor of the camera on which an object which is at a specific angle with respect to the optical axis of the camera is imaged, and to determine the corneal vertex distance as a difference between the second distance and the first distance.

\* \* \* \* \*

UNITED STATES PATENT AND TRADEMARK OFFICE
CERTIFICATE OF CORRECTION

| | | |
|---|---|---|
| PATENT NO. | : 11,747,651 B2 | Page 1 of 1 |
| APPLICATION NO. | : 18/056763 | |
| DATED | : September 5, 2023 | |
| INVENTOR(S) | : Jeremias Gromotka and Michael Gamperling | |

It is certified that error appears in the above-identified patent and that said Letters Patent is hereby corrected as shown below:

In the Specification

In Column 10, Line 63: change "Mitzi" to -- Nützi --

Signed and Sealed this
Second Day of January, 2024

Katherine Kelly Vidal
*Director of the United States Patent and Trademark Office*